(12) United States Patent
Mawhinney

(10) Patent No.: US 6,463,336 B1
(45) Date of Patent: Oct. 8, 2002

(54) ACTIVE BANDAGE SUITABLE FOR APPLYING PULSED RADIO-FREQUENCIES OR MICROWAVES TO THE SKIN FOR MEDICAL PURPOSES

(75) Inventor: Daniel D. Mawhinney, Livingston, NJ (US)

(73) Assignee: MMTC, INC, Princeton, NJ (US)

(*) Notice: Subject to any disclaimer, the term of this patent is extended or adjusted under 35 U.S.C. 154(b) by 0 days.

(21) Appl. No.: 09/283,971

(22) Filed: Apr. 1, 1999

(51) Int. Cl.[7] .................................................. A61N 1/00
(52) U.S. Cl. ...................... 607/156; 607/155; 607/103; 607/50; 600/14; 600/15
(58) Field of Search .............................. 607/3, 50, 103, 607/155, 156; 600/14, 15

(56) References Cited

U.S. PATENT DOCUMENTS

| | | | | |
|---|---|---|---|---|
| 4,932,420 A | * | 6/1990 | Goldstein | 607/156 |
| 4,982,742 A | * | 1/1991 | Claude | 607/50 |
| 5,101,836 A | * | 4/1992 | Lee | 607/155 |
| 5,314,401 A | * | 5/1994 | Tepper | 600/14 |
| 5,478,303 A | * | 12/1995 | Foley-Nolan et al. | 600/15 |
| 5,983,134 A | * | 11/1999 | Ostrow | 604/20 |
| 6,174,276 B1 | * | 1/2001 | Blackwell | 600/13 |
| 6,418,345 B1 | * | 7/2002 | Tepper et al. | 607/51 |

\* cited by examiner

*Primary Examiner*—Carl Layno
(74) *Attorney, Agent, or Firm*—George J. Seligsohn

(57) ABSTRACT

An active RF or microwave bandage, that incorporates any of various disclosed configurations of pliable planar microstrip or slotline antenna structures, is conformable to a selected area of the skin of a patient for use in therapeutically treating soft tissue of the patient underlying the selected area with pulsed electromagnetic field (PEMF) energy of a given frequency radiated from the planar antenna structure. The PEMF energy is supplied to the planar antenna structure by means including a PEMF generator (which generator may be a miniaturized portable generator employing a battery power supply that permits the patient being treated to be ambulatory).

16 Claims, 7 Drawing Sheets

ACTIVE BANDAGE SUITABLE FOR APPLYING PULSED RADIO-FREQUENCIES OR MICROWAVES TO THE SKIN FOR MEDICAL PURPOSES

BACKGROUND

1. Field of the Invention

The present invention relates to an active radio-frequency (RF) or microwave bandage which may be used for such medical therapeutic purposes as (1) promoting improved healing of soft-tissue wounds and incisions proximate to the skin of a patient and/or (2) enhancing the efficacy of transdermal drug delivery to a patient.

2. Description of the Prior Art

It is known that pulsed RF energy is helpful in treating a variety of injuries and diseases, including promoting the healing and regrowth of both bone and soft tissue injuries, and treating osteoarthritis, bursitis, and pelvic inflammatory disease. Usually, such treatments employ relatively low-frequency pulsed RF (e.g., 27.12 Mhz). In this regard, reference is made to the following articles in the literature:

1. M. J. Lobell, "Pulsed High Frequency and Routine Hospital Antibiotic Therapy in the Management of Pelvic Inflammatory Disease: A Preliminary Report", Clinical Medicine, August 1962.
2. B. M. Cameron, "Experimental Acceleration of Wound Healing", American Journal of Orthopedics, November 1961.
3. J. H. Goldin et al, "The Effects of Diapulse on the Healing of Wounds: A Double-Blind Randomised Controlled Trial in Man", British J. of Plastic Surgery, 34, 1981.
4. V. Barclay et al, "Treatment of Various Hand Injuries by Pulsed Electromagnetic Energy (Diapulse)", Physiotherapy, vol. 69, June 1983.
5. H. Itoh et al, "Accelerated Wound Healing of Pressure Ulcers by Pulsed High Peak Power Electromagnetic Energy (Diapulse)", Decubitus, February 1991.

It is also known that transdermal drug delivery may be used for local treatment of diseases of the skin, and also may be used with a small number of drugs for systemic drug delivery. The advantages of transdermal drug delivery over pills and injections include the avoidance of degradation due the gastrointestinal tract and first-pass of the liver, potential for steady or time controlled delivery of drugs, and targeted delivery to areas of diseased skin. Further, it is known that transdermal drug delivery can be enhanced by means of either pulsed DC electroporation or pulsed high power RF or microwave electroporation. In this regard, reference is made to the following articles in the literature:

6. M. R. Prausnitz et al, "Electroporation of Mammalian Skin: A mechanism to Enhance Transdermal Drug Delivery", Proc, Natl. Acad. Sci. USA, Vol. 90, pp 10504–10508, Medical Sciences, November 1993.
7. R. Vanbever et al, "Transdermal Delivery of Metropol by Electroporation", Pharmaceutical Research, Vol. 11, pp. 1657–1662, Nov. 11, 1994.
8. J. E. Riviere and M. C. Heit, "Electrically-Assisted Transdermal Drug Delivery", Pharmaceutical Research, Vol. 14, pp. 6g7–6g7, June 1997.
9. C. Domenge et al, "Antitumor Electrochemotherapy; New Advances in the Clinical Protocol", Cancer, Vol. 77, pp. 956–963, Mar. 1, 1996.
10. F. Sterzer, "Method for Enhancing Delivery of Chemotherapy Employing High-Frequency Force Fields", U.S. Pat. No. 5,368,837 Feb. 7, 1995.

Problems which now exist in the implementation of the treatments of the aforesaid prior art are that (1) Diapulse apparatus incorporates an RF generator having a permanently attached RF applicator which is in non-contacting spatial relationship with skin of a patient for radiating relatively low-frequency pulsed RF energy to the treated soft tissue underlying this skin and (2) electrical contacts have to be securely attached to the area of the patient to be treated (except for treating pressure ulcers, as described above in H. Itoh et al. (article 5)) and may have to be implanted in the patient. The discomfort to the patient of this type of implementation is particularly great in those cases in which the duration of the treatment must extend continuously over a relatively long time or must be repeated many times with a relatively short time interval between successive treatments.

Further, known in the art, are planar antenna structures that can consist of a microstrip configuration arranged in any one of various shapes of radiating elements. A microstrip planar antenna structure is fabricated from a printed circuit board by photoetching or micromachining a pre-metallized surface on one side of an insulated substrate with tightly controlled dimensions and dielectric constant in accordance with the particular shape of either a single one or an array of desired radiating elements. The proper frequency is determine by the dielectric constant of the substrate and the dimensions of each desired radiating element. Usually, the other side of the insulated substrate is also pre-metallized to provide a ground plane that functions as a reflector or a shield. Also, known in the art, is a planar antenna structure configured as a slotline antenna.

SUMMARY OF THE INVENTION

The active RF or microwave bandage of the present invention, which may employ any of various configurations of planar microstrip or slotline antenna structures, solves the implementation problem of the treatments of the aforesaid prior art by providing a practical, convenient, and effective means of implementation that would be both widely available to physicians and nurses and be much more comfortable to the patient. More specifically, the present invention is directed to an active bandage incorporating at least one pliable planar antenna that is conformable to a selected area of the skin of a patient for use in therapeutically treating soft tissue of the patient underlying the selected area with pulsed electromagnetic field (PEMF) energy of a given frequency radiated from the planar antenna. The PEMF energy is supplied to the planar antenna by means including a PEMF generator (which generator may be a miniaturized portable generator employing a battery power supply that permits the patient being treated to be ambulatory).

DESCRIPTION OF THE PREFERRED EMBODIMENTS

The objective of the present invention is to provide an RF or microwave PEMF delivery system including an active bandage for therapeutic purposes that include both (1) promoting improved healing of soft-tissue wounds and incisions proximate to the skin of a patient and/or (2) enhancing the efficacy of transdermal drug delivery to a patient. It is essential that this PEMF delivery system be safe for both the patient and the provider. In promoting improved healing, the PEMF delivery system must be flexible enough to cover a wide variety of wounds and injuries, including (but not limited to) operation incisions, treatment of pressure sores (especially bedsores for incapacitated individuals) and inflamed joints.

Figure 1:
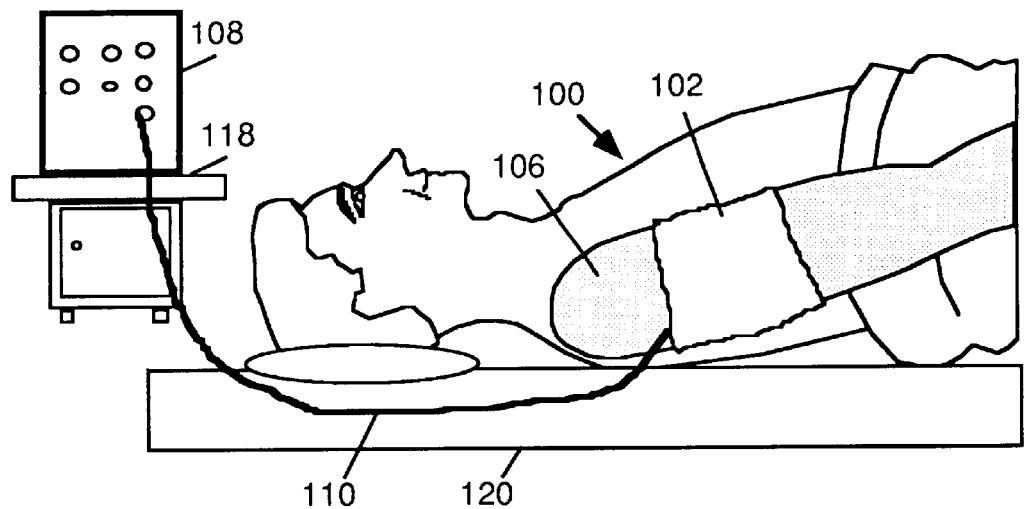
FIGS. 1 and 1a, together, diagrammatically illustrate an active RF bandage that includes a planar antenna (assumed to be configured as the microstrip antenna shown in FIG. 2), which antenna is being used to therapeutically irradiate a skin area of the arm of a patient with energy from a pulsed electromagnetic field (PEMF) generator.

For illustrative purposes, FIGS. 1 diagrammatically shows an RF or microwave PEMF delivery system for a patient 100 which comprises an active bandage 102 spatially situated in substantial contact with portion 104 (shown in FIG. 1a) of the skin of upper arm 106 of patient 100, together with PEMF generator 108 and coaxial cable 110 for applying pulsed RF or microwave frequency electromagnetic energy to portion 104 of the skin of upper arm 106 by means of planar antenna 112 (shown in FIG. 1a) incorporated in active bandage 102. It is assumed that active bandage 102 covers a wound in the upper arm 106 of patient 100 and that active bandage 102 is being employed to radiate the wound with pulsed electromagnetic frequency energy in order to promote healing of the wound.

Figure 1A:
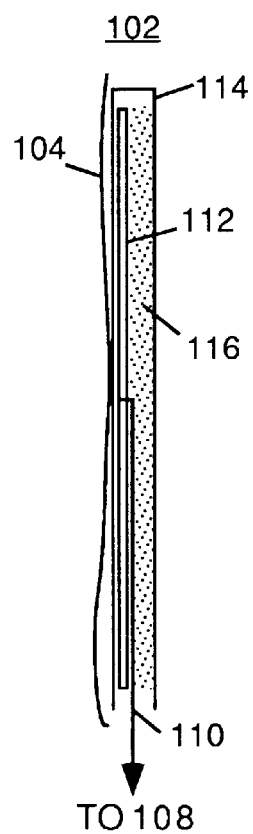

More specifically, as diagrammatically shown in FIG. 1a, active bandage 102 comprises envelope 114 (which may consist of commercially available TELFA® non-stick sterile pads through which blood or other liquid leaking from a wound can seep) within which planar antenna 112 and a liquid-absorbent material 116 (such as gauze) are situated. For illustrative purposes in FIG. 1a, planar antenna 112 is assumed to be configured as the microstrip antenna shown in FIGS. 2a and 2b (which is described in detail below), which has (1) a radiating front surface situated next to skin portion 104 of the wounded upper arm 106 of patient 100 and (2) a ground-plane back surface covered by liquid-absorbent material 116. The purpose of liquid-absorbent material 116 (which preferably is affixed to the back of planar antenna 112) is to absorb seepage from the wound in a manner more fully discussed below in the description of FIGS. 2a and 2b.

As further shown in FIG. 1a, the inner conductor of coaxial cable 110 is connected to the radiating front surface of planar antenna 112 through a central hole therethrough and has the outer conductor of coaxial cable 110 connected to the ground-plane back surface of planar antenna 112. The outer layer of active bandage 102 shown in FIG. 1 preferably comprises a PEMF power absorbent material (as differentiated from a liquid absorbent material) and/or a metallic surface material to minimize RF or microwave leakage and contain the RF or microwave energy to the area being treated. Generalizing, an active bandage may comprise other unshown bandage components for securing the active bandage to the skin of the patient (e.g., tape, "Velcro", elastic bandage or other securing means). In this latter case, it is preferred that the outer layer of such unshown bandage component comprises a power absorbent material and/or a metallic surface material to provide shielding.

The Federal Communication Commission (FCC) has allocated RF frequencies within the 915 MHz frequency band and microwave frequencies within the 2450 Mhz frequency band for Industrial, Scientific, Medical (ISM) purposes. Both the allocated RF frequencies of 915 MHz and microwave frequencies of 2450 Mhz are suitable for PEMF use. The advantage of using RF frequencies of 915 MHz is that the components are somewhat less expensive than 2450 Mhz components. However, 2450 Mhz components have the advantages that the antenna-applicators are inherently smaller and the pulsed electromagnetic fields penetrate less deeply into tissues. Thus active bandages made for the of 915 Mhz RF frequency band would be more suitable in most cases where a large area is to be covered or where a significant portion of the afflicted volume is below the surface (exemplified by long incisions, pressure ulcers and joint inflammations). However, active bandages made for the 2450 Mhz microwave frequency band would be more suitable for small wounds and spot rashes and inflammations caused by surgical excisions, cuts, punctures, and localized allergic reactions. An otherwise unallocated frequency within the 915 Mhz RF frequency band or the 2450 Mhz microwave frequency band should be selected as the operating frequency for active-bandage use in order to shield the active bandage adequately to comply with all FCC requirements for that frequency band.

For therapeutic purposes, the peak power of each of the PEMF pulses should be relatively high, but the average power should be sufficiently low so that, depending on the particular therapeutic purpose, tissue heating is either negligible or, alternatively, is limited to some certain desired safe temperature. Therefore, the peak and average power of the output from PEMF generator 108 is set in accordance with such therapeutic purposes. For instance, by way of one example for the case in which active bandage is made for the 915 Mhz RF frequency band, the peak power of each pulse may be set in the order of 57 watts, the pulse width may be set at 42 µs and the pulse repetition rate may be set at 0.5 kHz. This results in a duty cycle of only 2.1% and an average power of only 1.197 watts, resulting in moderate heating of the irradiated tissue of the patient.

Generalizing, moderate heating of the irradiated tissue of the patient to a safe temperature of about 39° C. is often desirable because it produces additional beneficial therapeutic effects by increasing blood flow to the tissues heated by RF or microwave PEMF radiation emitted by the planar antenna of the active bandage. Further, because the activity of many drugs is enhanced at elevated temperatures, the uptake of drugs that promote healing may be increased by the treated tissue of the patient absorbing the RF or microwave PEMF radiation emitted by the planar antenna of the active bandage. In addition, the treatment depth of the irradiated tissue can be adjusted to match the depth of the wound by adjusting the frequency of the PEMF generator. Specifically, the particular frequency within the 915 Mhz RF frequency band (which is utilized for relatively deep wounds) may be finely tuned to match the depth of a given deep wound, while the particular frequency within the 2450 Mhz microwave frequency band (which is utilized for relatively shallow wounds) may be finely tuned to match the depth of a given shallow wound. Further, the shape, size and geometry of the planar antenna of the of the active bandage should be chosen to efficiently emit a localized radiation field which is to a large extent is confined to solely the affected tissue volume of the wound, thereby minimizing the undesired irradiation of non-affected tissue. Various embodiments of a planar-antenna structure suitable for use as a component of an active bandage are diagrammatically shown, respectively, in (1) FIGS. 2a and 2b, (2) FIGS. 3a and 3b, (3) FIG. 4a and 4b, (4) FIG. 5a and 5b, (5) FIGS. 6a, 6b and 6c, and (6) FIGS. 7a, 7b and 7c.

Figure 2A:
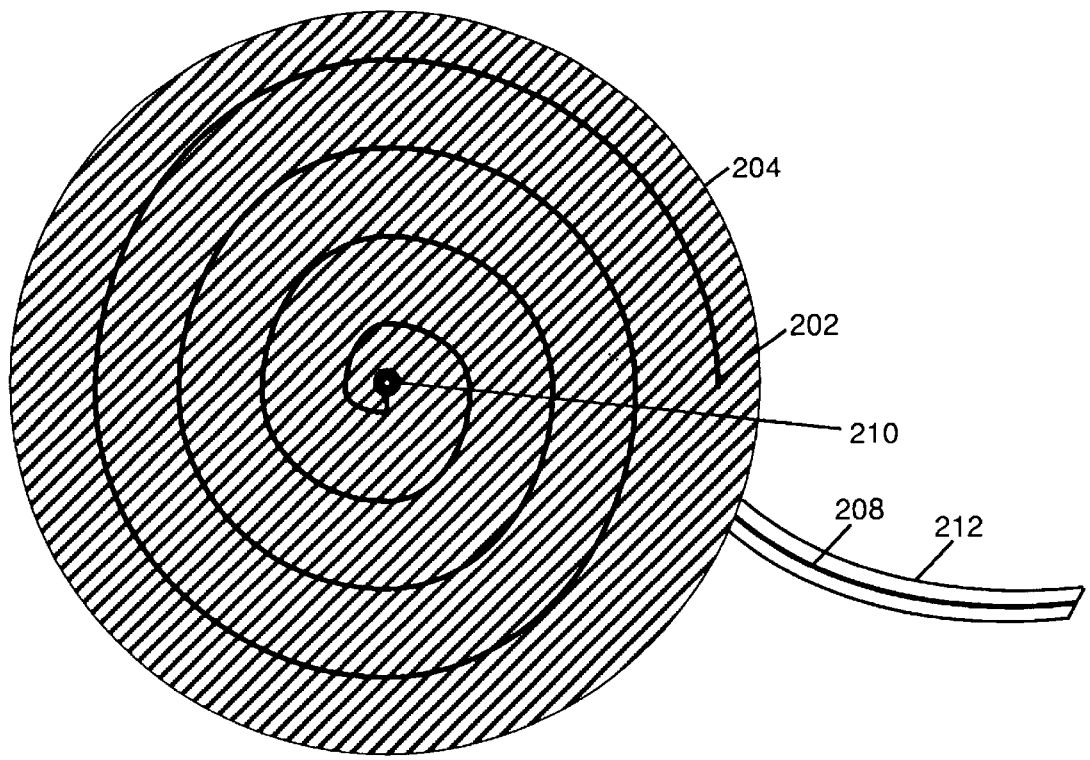
FIGS. 2a and 2b, together, illustrate a first preferred embodiment of a planar microstrip antenna having a radiating surface configured substantially as a circular spiral suitable for use as a component of the active RF or microwave bandage of FIG. 1
Figure 2C:
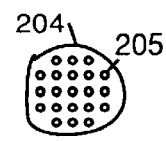
FIG. 2c shows a species of this first preferred embodiment in which the substrate of the planar microstrip antenna includes many small perforations therethrough.
Figure 2B:
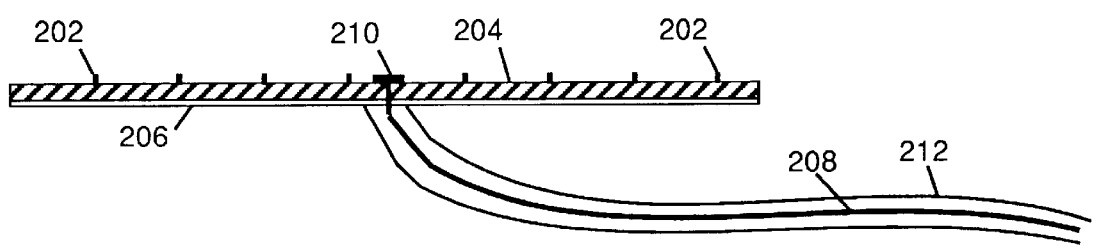

Referring now to FIG. 2a (which is a plan view) and FIG. 2b (which is an edge view), there is shown planar microstrip antenna 200 having a metallic radiating surface 202 configured substantially as a circular spiral line. Specifically, planar microstrip antenna 200 comprises thin pliable dielectric substrate 204 (shown in the drawing as cross-hatched), having circular-spiral metallic line radiating surface 202 (shown in the drawing as black) clad on a portion of the front side of dielectric substrate 204 and metallic ground plane 206 (shown in the drawing as white) clad on substantially the entire back side of dielectric substrate 204. Although not essential, it is assumed that substrate 204 includes many small perforations 205 (shown in FIG. 2c) therethrough which permit blood or other liquid wound leakage to reach and be absorbed by liquid-absorbent material 116 (e.g., gauze shown in FIG. 1a) that is preferably affixed to the back side of planar microstrip antenna 200. Inner conductor 208 of a miniature coaxial cable from a PEMF generator is connected to centrally-located terminal 210 of circular-spiral metallic line radiating surface 202 through a central hole through dielectric member 204 and outer conductor 212 of this coaxial cable is connected directly to metallic ground plane 206 as shown in FIGS. 2a and 2b.

Preferably, planar microstrip antenna 200 is fabricated from a 0.3 mm thick pliable panel of RT/duroid 5880®laminate. RT/duroid 5880 laminate is a glass microfiber reinforced polytetrafluoroethylene (PTFE) composite, which is clad on both its front and back sides with a thin layer (e.g., $\frac{1}{8}$ to 2 ounces/ft$^2$) of electro-deposited copper. Circular-spiral line radiating surface 202 is prepared by employing an appropriate mask to selectively etch away unwanted portions of the front-side copper-clad layer of the RT/duroid 5880 laminate. One of the desirable properties of a 0.3 mm thick copper-clad panel of RT/duroid 5880 laminate is that it is flexible enough to be easily shaped to conform reasonably well to uneven surfaces of a patient's body, including such uneven surfaces as elbows and knees.

The resonant frequency of planar microstrip antenna 200 depends on such factors as the diameter size of antenna 200, the number of turns of circular-spiral metallic line of radiating surface 202 (i.e., the total spiral line-length thereof) and the spacing between adjacent turns of circular-spiral metallic line of radiating surface 202. For instance, two separate design examples of the diameter size suitable for antenna 200 are a 1-inch diameter size and a 2.5-inch diameter size. By cutting the printed length of the spiral line of radiating surface 202, the resonant frequency of planar microstrip antenna 200 may be tuned to a particular operating frequency. This is true because the spiral line of radiating surface 202 is a multiple number of wavelengths at any frequency within the frequency band being used. If the PEMF generator operates at a certain fixed frequency, the resonant frequency of planar microstrip antenna 200 may be tuned to this certain fixed frequency. Alternatively, if the frequency of the PEMF generator is tunable, this resonant frequency may be tuned to best match the load impedance presented by the patient's tissue being treated. Therefore, a simple means of selecting a desired optimum operating frequency within the frequency band being used is to shorten the spiral line of radiating surface 202 until the resonant frequency is tuned to this desired optimum operating frequency.

Further, the design spiral shape of the radiating surface of antenna 200 is not limited to the circular spiral line shape shown in FIGS. 2a and 2b. For instance, the spiral line radiating surface of antenna 200 could have some other design spiral shape (such as of a rectangular spiral shape, rather than a circular spiral shape). In any case, antenna 200, having a spiral line radiating surface 202, constitutes a first preferred embodiment of a planar microstrip antenna is most suitable for use as a component of an active RF or microwave bandage which treats those type of soft-tissue areas having approximately equal length and width dimensions.

Figure 3A:
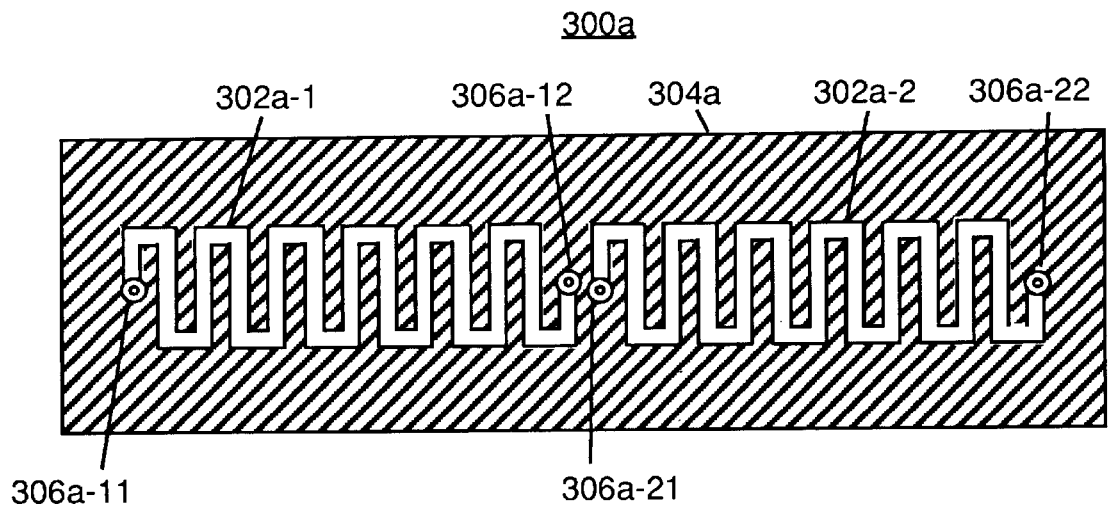
FIGS. 3a and 3b, respectively, illustrate a first example, comprising a meander line, and a second example, comprising a folded dipole, of a second preferred embodiment of a planar microstrip antenna that is configured as a longitudinal radiating surface which is suitable for use as a component of an active RF or microwave bandage.
Figure 3B:
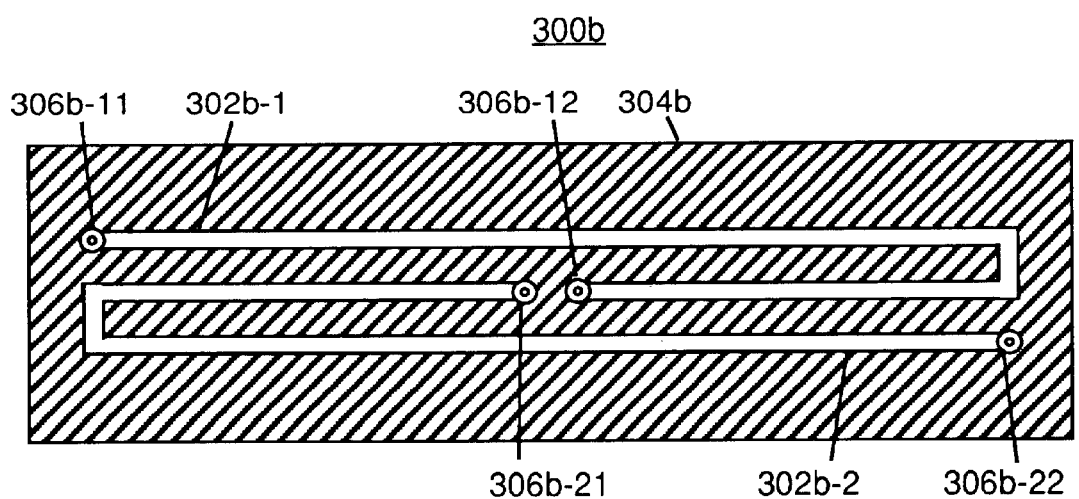

An active RF or microwave bandage which is suitable for use in treating linear wounds, such as incisions from surgical procedures, requires a planar microstrip antenna comprising a longitudinal radiating surface. In this regard, reference is now made to FIGS. 3a and 3b. FIG. 3a diagrammatically shows planar microstrip antenna 300a comprising a metallic longitudinal radiating surface configured as two meander-line halves 302a-1 and 302a-2 (shown in white) clad on a portion of the front side of thin dielectric substrate 304a (shown in the drawing as cross-hatched) and entirely clad on its back side with an unshown ground plane. This meander-line configuration constitutes a first example of a second preferred embodiment of a planar microstrip antenna suitable for use as a component of an active RF or microwave bandage. FIG. 3b diagrammatically shows planar microstrip antenna 300b comprising a metallic longitudinal radiating surface configured as two folded-dipole halves 302b-1 and 302b-2 clad on a portion of the front side of thin dielectric substrate 304b and entirely clad on its back side with an unshown ground plane. This folded-dipole configuration constitutes a second example of the second preferred embodiment of a planar microstrip antenna suitable for use as a component of an active RF or microwave bandage. Each of dielectric substrates 304a and 304b, like dielectric substrate 204, is preferably fabricated from a 0.3 mm thick panel of RT/duroid 5880® laminate.

Also shown in FIG. 3a are terminals 306a-11 and 306a-12, connected to the opposite ends of meander-line half 302a-1, and terminals 306a-21 and 306a-22, connected to the opposite ends of meander-line half 302a-2. This alternatively permits (1) a meander line comprising serially-connected meander-line halves 302a-1 and 302a-2 to be end fed from the left with PEMF energy by coupling a coaxial line from the output of a PEMF generator to terminal 306a-11 and serially-connecting terminal 306a-12 to 306a-

21; (2) a meander line comprising serially-connected meander-line halves 302a-1 and 302a-2 to be end fed from the right with PEMF energy by coupling a coaxial line from the output of a PEMF generator to terminal 306a-22 and serially-connecting terminal 306a-21 to 306a-12, or (3) a meander line comprising serially-connected meander-line halves 302a-1 and 302a-2 to be center fed with PEMF energy by coupling a balanced line from the output of a PEMF generator to terminals 306a-11 and 306a-21.

As shown in FIG. 3b, terminals 306b-11 and 306b-12, which are connected to opposite ends of folded-dipole half 302b-1, and terminals 306b-21 and 306b-22, which are connected to opposite ends of folded-dipole half 302b-2, permit the output of the PEMF generator to feed PEMF energy to a folded dipole composed of folded-dipole halves 302b-1 and 302b-2 in any of the same three ways that the above-described meander line comprising meander-line halves 302a-1 and 302a-2 is fed from the output of a PEMF generator.

Further, it is feasible to design any desired regular or irregular length and longitudinal shape for a radiating surface configured as either meander line halves 302a-1 and 302a-2 or folded dipole 302b-1 and 302b-2 to better match the shape of a patient's incision, since the ability to cut either of such radiating surfaces to a desired number of multiple wavelengths (as described above) can be used to eliminate the normal frequency/antenna dimension constraint.

Figures 4A, 4B:
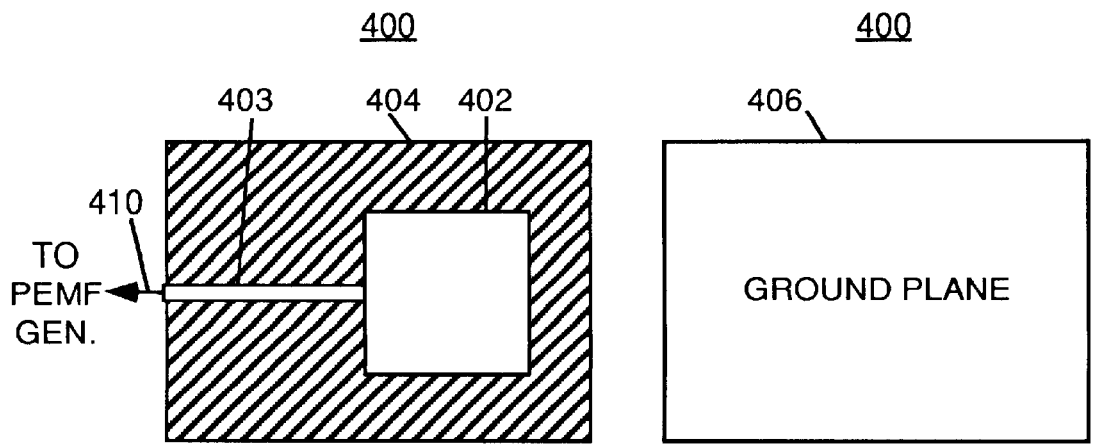
FIGS. 4a and 4b, together, illustrate a third preferred embodiment of a planar microstrip antenna having a radiating surface configured as a single patch which is suitable for use as a component of an active RF or microwave bandage.
Figure 5A:
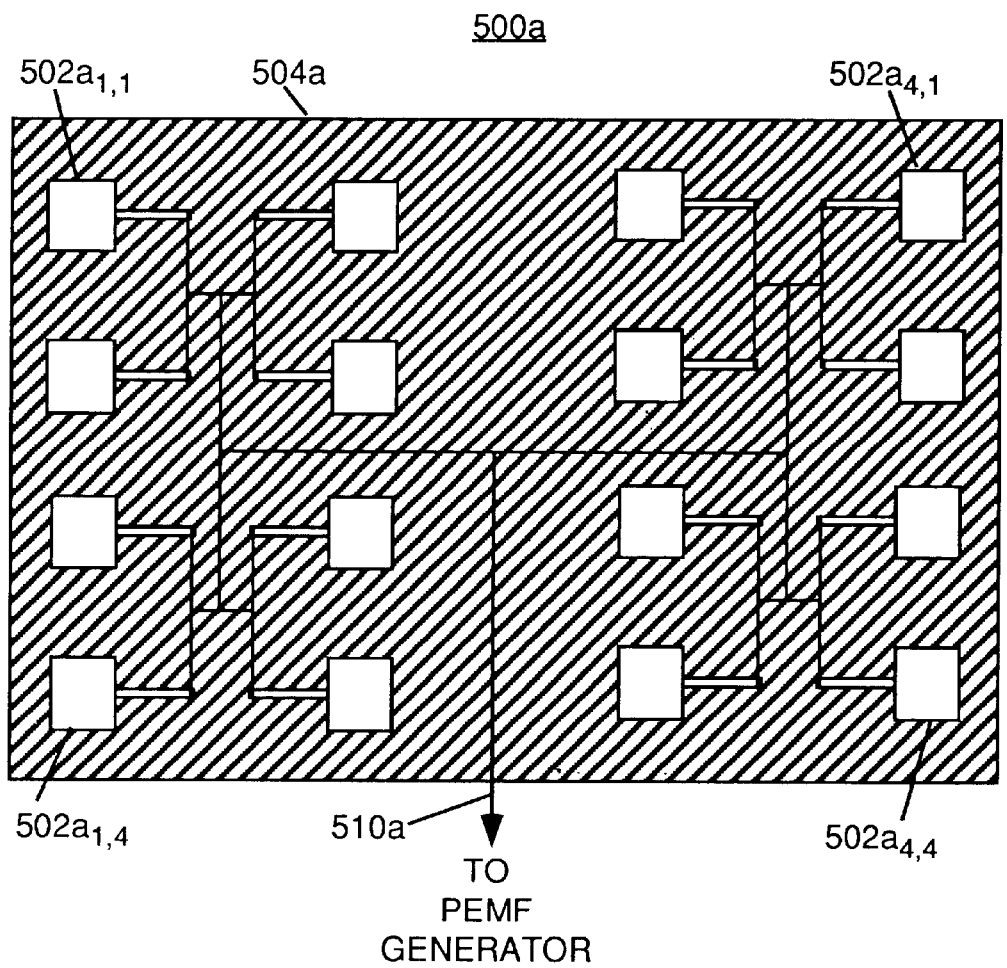
FIGS. 5a and 5b, respectively, illustrate first and second examples of a fourth preferred embodiment of planar microstrip antenna which is also suitable for use as a component of an active RF or microwave bandage, wherein the radiating surface is configured as a spatial array of a plurality of separate patches.
Figure 5B:
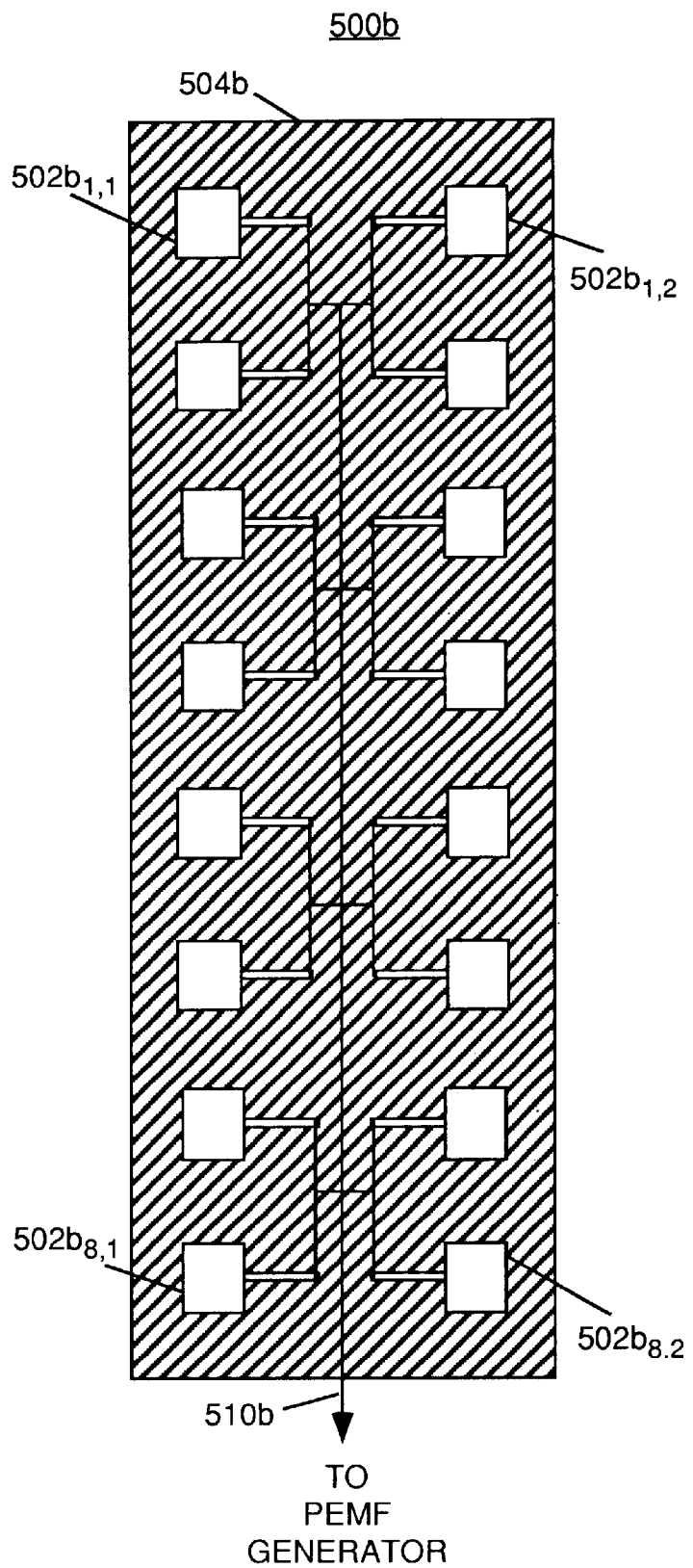

FIGS. 4a and 4b, together, illustrate a third preferred embodiment of a planar microstrip antenna 400 which is also suitable for use as a component of an active RF or microwave bandage. Specifically, as shown in FIG. 4a, planar microstrip antenna 400 comprises a metallic radiating surface (shown in the drawing as white) configured substantially as a single patch 402 and feed line 403 which is clad on a portion of the front side of thin dielectric substrate 404 (shown in the drawing as cross-hatched). Dielectric substrate 404, like dielectric substrate 204, is preferably fabricated from a 0.3 mm thick panel of RT/duroid 5880® laminate. As shown in FIG. 4b, the entire back side of dielectric substrate 404 is clad with metallic ground plane 406 (shown in the drawing as white). RF or microwave power from a PEMF generator may be coupled to patch 402 of planar microstrip antenna 400 through feed line 403 by means of coaxial cable 410 (which is schematically shown in FIG. 4a).

While, for illustrative purposes, the shape of patch 402 shown in FIG. 4a is configured as a square, it should be understood that, in practice, the shape of the patch of a planar microstrip antenna may have some other configuration, such as a circular shape, for instance.

An active bandage incorpotating a planar microstrip antenna comprising a single patch, such as patch 402, is well suited in its use to the treatments that involve only a small area of the skin (e.g., small wounds, and spot rashes and inflammations caused by surgical excisions, cuts, punctures, and localized allergic reactions). For such small-area treatments, the operating frequency of the PEMF generator usually will be within the relatively high 2450-MHz frequency band, rather than within the relatively low 915-MHz frequency band. Unlike the above-described cases of the first and second preferred embodiments of the present invention, it is not possible to tune the resonant frequency of a patch planar antenna by line cutting. Therefore, the dimensions of the patch, such as patch 402, should preferably be selected to match its resonant frequency to the optimum therapeutic operating frequency of the PEMF generator.

The present invention also contemplates, as a fourth preferred embodiment, an active bandage incorporating a planar microstrip antenna comprising an array consisting of a plurality of patches capable of treating a larger-area wound which matches the shape of the wound. In this regard, first and second examples of varying shapes of such a patch array are diagrammatically shown in FIGS. 5a and 5b. In particular, planar microstrip antenna 500a of FIG. 5a comprises a nominally 4×4 square-shape patch array consisting of the 16 patches $502a_{1,1}$ to $502a_{4,4}$ clad on dielectric substrate 504a to treat larger-area wounds that have approximately equal length and width dimensions. Alternatively, planar microstrip antenna 500b of FIG. 5b comprises an 8×2 narrow rectangular-shape patch array consisting of the 16 patches $502b_{1,1}$ to $502b_{8,2}$ clad on dielectric substrate 504b to treat long but narrow wounds, such as surgical incisions. Although not shown, a planar microstrip antenna comprising a patch array consisting of circular arrangement of patches would be suitable for treating area wounds such as bums.

The 16 patches of either the array of planar microstrip antenna 500a may be driven using a corporate feed 510a or, alternatively, the array of planar microstrip antenna 500b may be driven using a corporate feed 510b, which corporate feeds distribute the pulsed RF or microwave energy more or less equally to each patch of the respective arrays, while maintaining a proper impedance match for the PEMF generator.

Further, the present invention contemplates first and second embodiments of planar slotline antennas, either of which still may be useful as a component of an active RF or microwave bandage, although neither embodiment of these planar slotline antennas is to be preferred for such use.

Figure 6C:
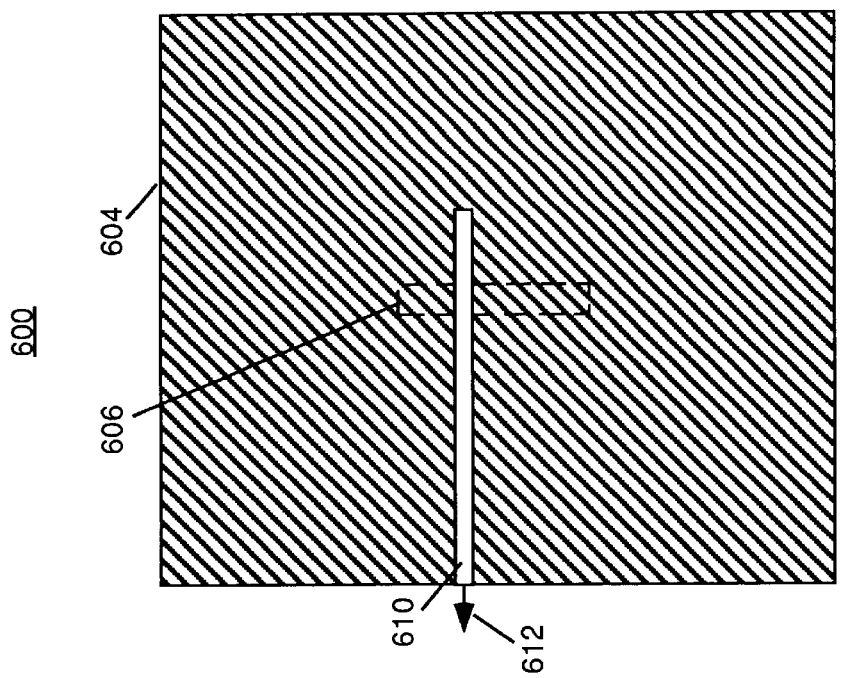
FIGS. 6a, 6b and 6c, together, illustrate a first non-preferred embodiment of a planar slotline antenna which still may be useful as a component of an active RF or microwave bandage.
Figure 6B:
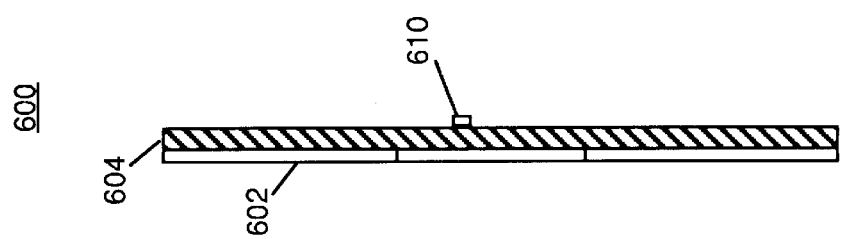
Figure 6A:
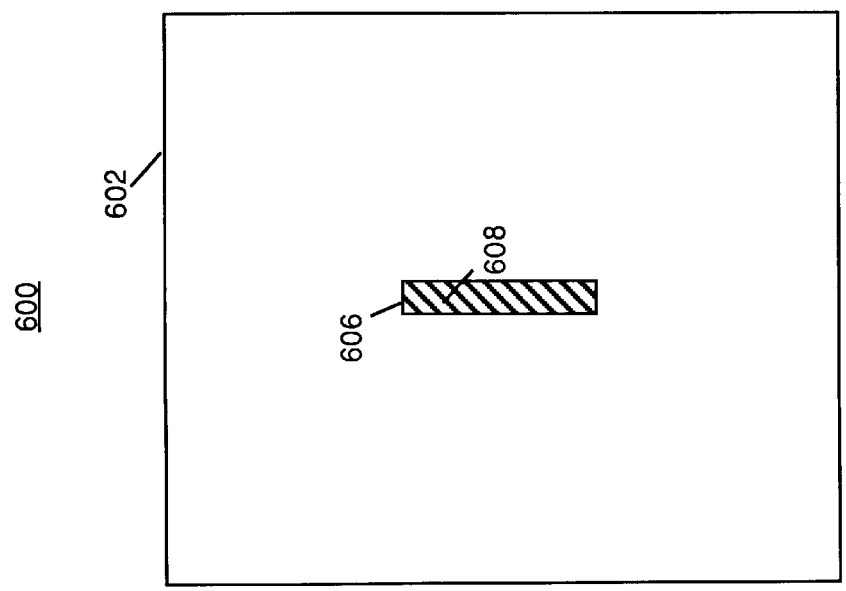

FIGS. 6a, 6b and 6c, together, diagrammatically show the structure of planar slotline antenna 600, which constitutes the first embodiment of planar slotline antennas. As shown, planar slotline antenna 600 comprises metallic ground plane 602 clad on the front side of dielectric substrate 604, with ground plane 602 including slot 606 therein through which portion 608 of the front side of dielectric substrate 604 is exposed. Metallic feed line 610, which is clad on the back side of dielectric substrate 604 in cooperative spatial relationship with slot 606, has RF or microwave power from a PEMF generator coupled thereto by means of coaxial cable 612.

A disadvantage in the use of planar slotline antenna 600 as a component of an active RF or microwave bandage, compared to the above-described planar microstrip antennas, is that the back side of dielectric substrate 604 is not shielded by a ground plane. Thus, uncontrollable interaction between slotline antenna 600 and external matter, including both movable parts of the patient's body and other relatively movable material in the vicinity of slotline antenna 600, tends to detune slotline antenna 600 and cause some mismatching between slotline antenna 600 and the patient's tissue being treated.

Figure 7C:
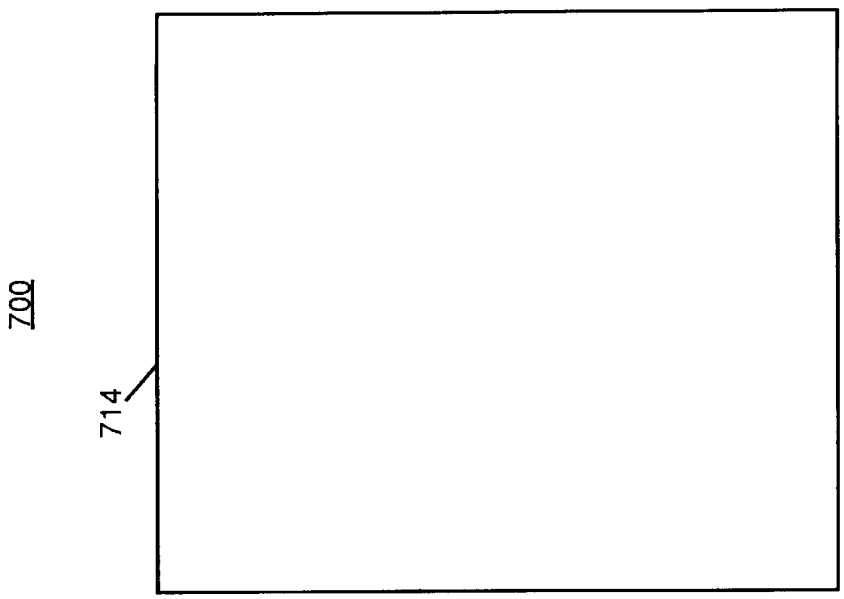
FIGS. 7a, 7b and 7c, together, illustrate a second non-preferred embodiment of a planar slotline antenna which still may be useful as a component of an active RF or microwave bandage.
Figure 7B:
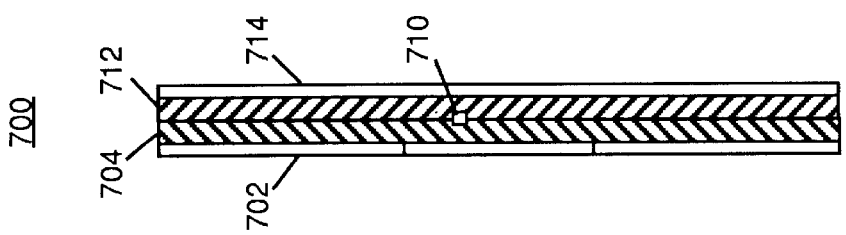
Figure 7A:
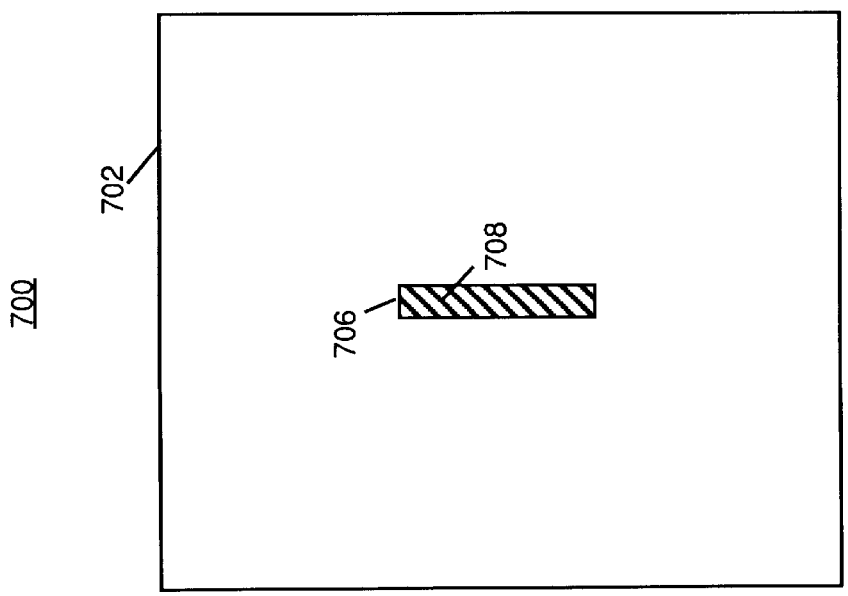

The aforesaid structural disadvantage of planar slotline antenna 600 may be overcome by employing the structure of planar slotline antenna 700, diagrammatically shown in FIGS. 7a, 7b and 7c, which together constitute the second embodiment of planar slotline antennas. Elements 702, 704, 706, 708 and 710 of FIGS. 7a, 7b and 7c structurally and functionally correspond, respectively, with elements 602, 604, 606, 608 and 610 of FIGS. 6a, 6b and 6c. Further, slotline antenna 700 also includes additional dielectric substrate 714 having (1) the front side of dielectric substrate 714 bonded to the back side of dielectric substrate 704 plane (thereby sandwiching feed line 710 between dielectric substrates 704 and 714) and (2) the back side of dielectric substrate 714 entirely clad with ground plane 716. This results in the structure of planar slotline antenna 700 being relatively thick, compared to the above-described planar microstrip antennas, which thickness may be considered to be a disadvantage in the use of planar slotline antenna 700 as a component of an active RF or microwave bandage.

Referring back to FIG. 1, PEMF generator 108, solely for illustrative purposes, is diagrammatically shown therein as being relatively large and being supported by relatively large fixed station unit 118, while, solely for illustrative purposes, patient 100 is diagrammatically shown therein as lying on bed 120. In general, such a fixed station unit having a size in the order of PEMF generator 108, would find most use as a bedside or chairside unit connected by coaxial cable 110 to patient 100. However, since the average power that generated by PEMF generator 108 is relatively low, it still is not excessively large or heavy. Further, auxiliary features, such as programmers and timers, can be incorporated without making the equipment unwieldy. In addition, it is necessary to comply with all safety requirements to assure that patient 100 cannot be subjected to an electrical hazard. To make sure of this, the equipment is designed to operate from low voltage DC provided from an approved isolated plug-in AC/DC converter, so that PEMF generator 108 will be fully isolated from the AC power lines, and also patient 100 will be doubly isolated because the active bandage 102 applicator will be isolated from the PEMF generator, since coaxial cable 110 does not employ any DC connection between PEMF generator 108 and the active bandage 102 applicator.

However, it should be understood that the diagrammatic showing in FIG. 1 is not intended to limit the scope of the present invention. For instance, the present invention contemplates the use of portable PEMF generators designed as compact and light-weight modules that can be carried about by an ambulatory patient or used for convenience by those who may be in wheelchairs or have limited mobility. Such a portable PEMF generator would be fully battery operated (rechargeable) and designed to operate for the periods of time needed for effective treatment. Since the moderately high peak powers required for successful RF or microwave PEMF treatments can be supplied at very low pulsed duty cycles (percentage of actual on time), the average power requirements are within feasible battery limits. Although a portable PEMF generator will not have some of the programming features and monitoring capabilities of a fixed station model, it still will be capable of providing a peak power level necessary for effective treatment, while being completely safe to use. However, such a portable PEMF generator would include a pre-settable programming to set up treatment conditions and indicators to show the status of the portable PEMF generator including proper function and battery status. Preferably, the structure of a portable PEMF generator should be miniaturized so that it can be incorporated into the active bandage itself, thereby obviating the need for an external coaxial-cable connection between the portable PEMF generator and the active PEMF bandage. With such a miniaturized portable PEMF generator, the only connections between will be the battery or other DC power source wires extending the distance between the active bandage and the battery or other DC power source. Since the battery or other DC power source would normally be attached to an ambulatory patient or, at least, be located very near such a patient, this is a trivial consideration.

While only certain configurations of planar antennas, that are suitable for incorporation in RF or microwave PEMF active bandages which may be used for medical therapeutic purposes, have been shown in the drawing FIGURES. and specifically described herein, it should be understood that the present invention is not limited to RF or microwave PEMF active bandages incorporating these certain configurations of planar antennas, but includes any configuration or modification of a single planar antenna or a spatial array of a plurality of planar antennas suitable for incorporation in an RF or microwave PEMF active bandage which may be used for medical therapeutic purposes.

Further, any of various known techniques useful in the irradiation of selected tissue of a patient with RF or microwave energy can be useful in connection with an RF or microwave PEMF active bandage. For example, a temperature sensing probe may be incorporated in the PEMF active bandage to monitor wound temperature and (1) cause a power cutoff mechanism in the PEMF generator to be operated in response to an unsafe temperature being reached and (2) with the PEMF generator unoperated, employ the monitored wound temperature to sense healing or detect infection. Another example would be to include known means responsive to the value of reflected power from the irradiated tissue of the patient to automatically tune the operating frequency of the PEMF generator to that frequency that minimizes the value of the reflected power.

Further, an RF or microwave PEMF active bandage of the present invention which may be used for medical therapeutic purposes exhibits one or more of the following nine beneficial properties 1. The active bandage makes contact with the patient and can be conformal. This concentrates the RF or microwave energy allowing lower powers to be used for safety and efficiency.
2. Much higher frequencies can be used than those used for either diathermy or Diapulse PEMF (e.g., 27 MHz) This enables the use of smaller antennas that can better localize the RF or microwave energy and control the degree of penetration to restrict treatment to a specific volume.
3. Different frequencies can be selected. This enables matching the bandage to the size and depth of the wound improving the overall safety and lowering the power levels required.
4. Lower power requirements for effective treatment. This makes the use of smaller and portable solid-state RF or microwave PEMF generators viable making it possible to operate on batteries and be patient portable.
5. The active bandage can be combined with conventional wound dressings. The combined active bandage/dressing can be disposable since it will not be a costly item since the RF or microwave PEMF generator is normally connected by cable.
6. The patient can be mobile while wearing the active bandage. The small size of the active bandage and the conformal contact arrangement will allow the patient considerable freedom to move about, eat, sleep, and be attended by medical personnel and otherwise treated without interference.
7. Any number of separate wounds can be treated simultaneously. The active bandages will be relatively small and a number of them can be applied even in close proximity without interaction. A common PEMF generator with multiple outputs or a single time multiplexed output could be provided.
8. Automatic tuning for optimal antenna match can be incorporated Since the relative position of the active bandage on the patient is fixed, the antenna can be optimally matched by monitoring the reflected power and tuning impedance matching elements in the PEMF generator.

9. The active bandage can be attached in a number of ways and easily shielded. Adhesive tape, elastic bandages, Velcro, wrap-around techniques are all applicable. The outer layer can be a power absorbent material (as differentiated from a liquid absorbent material) and/or a metallic surface material to minimize RF or microwave leakage and contain the RF or microwave energy to the area being treated.

What is claimed is:

1. An article of manufacture comprising an active bandage incorporating at least one pliable planar antenna that is conformable to a selected area of the skin of a patient for use in deriving a radiation pattern for therapeutically treating soft tissue of the patient underlying said selected area with pulsed electromagnetic field (PEMF) energy of a given frequency within a given one of the 915 MHz frequency band and the 2450 MHz frequency band radiated from said planar antenna for a purpose which includes (1) promoting improved healing of soft-tissue wounds and incisions proximate to said selected area of the skin of said patient and/or (2) enhancing the efficacy of transdermal drug delivery to said soft tissue of the patient underlying said selected area of the skin of said patient, wherein said pliable planar antenna comprises a pliable dielectric panel having a given dielectric constant, which panel (1) has a first metallic clad having a first given configuration of first given dimensions disposed over a back surface thereof intended to be disposed distal to said selected area of the skin and (2) has a second metallic clad having a second given configuration of second given dimensions disposed over a front surface thereof intended to be disposed proximate to said selected area of the skin, whereby said radiation pattern is determined by said first and second given configurations, the respective values of said first and second given dimensions and the value of said given dielectric constant, and the respective values of said given dielectric constant and said second given dimensions are such as to result in substantial matching of said pliable planar antenna at said given frequency.

2. The article of manufacture defined in claim 1, wherein:

said active bandage comprises an outer layer made of a PEMF power absorbent material to minimize PEMF energy leakage from said active bandage and contain the PEMF energy to said selected area of the skin of said patient being treated.

3. The article of manufacture defined in claim 1, wherein:

said active bandage comprises an outer layer made of a metallic surface material that provides shielding to minimize PEMF energy leakage from said active bandage and contain the PEMF energy to said selected area of the skin of said patient being treated.

4. The article of manufacture defined in claim 1, wherein:

said pliable planar antenna is a microstrip planar antenna in which said first metallic clad comprises a ground plane of said microstrip planar antenna and said second metallic clad comprises a radiating element in which said second configuration is a given one of a substantially spiral configuration, a substantially meander-line configuration, a substantially folded-dipole configuration and a substantially patch configuration, and the respective values of said given dielectric constant and the given dimensions of said radiating element are such as to result in said metallic radiating element being substantially matched at said given frequency.

5. The article of manufacture defined in claim 4, wherein said active bandage incorporates a plurality of pliable microstrip planar antennas that are conformable to said selected area of the skin of said patient and wherein:

said pliable dielectric panel having said given dielectric constant, and said first metallic clad comprising said ground plane is common to said plurality of pliable microstrip planar antennas;

said second metallic clad comprises a plurality of spaced, corporately-fed radiating elements all of which have said given one of said second configurations distributed over said front surface, wherein each of said plurality of radiating elements individually corresponds to each of said plurality of pliable microstrip planar antennas.

6. The article of manufacture defined in claim 5, wherein:

said given one of said second configurations of all said radiating elements is a patch configuration.

7. The article of manufacture defined in claim 1, wherein:

said pliable planar antenna is a slotline antenna in which (1) said second metallic clad comprises a metallic ground plane with a slot of given-area dimensions cut through both said ground plane and said dielectric panel and (2) said first metallic clad on its back side comprises a metallic feed line clad which is located in cooperative spatial relationship with said slot.

8. The article of manufacture defined in claim 7, wherein:

said slotline antenna further comprises another pliable dielectric panel having (3) its front side bonded to the back side of said first-mentioned dielectric panel to thereby sandwich said metallic feed line in between said first-mentioned and said other dielectric panels, and (4) its back side clad with a second metallic ground plane.

9. The article of manufacture defined in claim 1, wherein:

said active bandage further incorporates liquid-absorbent material positioned in a location directly behind said back surface of said dielectric panel for absorbing liquid leakage from said selected area of the skin of said patient .

10. The article of manufacture defined in claim 9, wherein:

said liquid-absorbent material comprises gauze.

11. The article of manufacture defined in claim 9, wherein:

said liquid-absorbent material is affixed to said back surface of said dielectric panel.

12. The article of manufacture defined in claim 9, wherein said active bandage further incorporates:

an envelope being composed of a material which is (1) porous to said liquid leakage from said selected area of the skin of said patient and (2) is substantially non-absorbent of radiation emitted by said planar antenna within which said planar antenna and said liquid-absorbent material are situated.

13. The article of manufacture defined in claim 9, wherein:

said dielectric panel is perforated to enhance seepage of said liquid leakage from said selected area of the skin of said patient through said dielectric panel to said liquid-absorbent material.

14. In apparatus for therapeutically treating soft tissue of a patient underlying a selected area of the patient's skin with pulsed electromagnetic field (PEMF) energy of a given frequency within a given one of the 915 MHz frequency band and the 2450 MHz frequency band for a purpose which includes (1) promoting improved healing of soft-tissue wounds and incisions proximate to said selected area of the skin of said patient and/or (2) enhancing the efficacy of transdermal drug delivery to said soft tissue of the patient underlying said selected area of the skin of said patient, wherein said apparatus comprises in combination:

an active bandage incorporating at least one pliable planar antenna that is conformed to said selected area of the skin of said patient for use in deriving a radiation pattern of said PEMF energy of said given frequency within said given one of the 915 MHz frequency band and the 2450 MHz frequency band which irradiates said soft tissue with said PEMF energy radiated from said planar antenna in response to said pliable planar antenna being supplied with a given limited amount of pulsed energy at said given frequency; and means including a generator for supplying said given limited amount of pulsed energy at said given frequency from said generator to said pliable planar antenna, wherein said given limited amount of pulsed energy has a value which is insufficient to heat said irradiated soft tissue to a temperature higher than 39° C.

15. The apparatus defined in claim 14 wherein:

said given frequency from said generator is in the 915 MHz frequency band, band, the peak power of each pulse is substantially of 57 watts, the pulse width is substantially 42 $\mu$s and the pulse repetition rate is substantially 0.5 kHz;

whereby there results a duty cycle of substantially 2.1% and an average power of substantially 1.197 watts.

16. The apparatus defined in claim 14, wherein:

said given limited amount of pulsed energy has a value which is sufficiently low as to result in only negligible heating of said irradiated soft tissue.

\* \* \* \* \*